United States Patent
Thijs et al.

(10) Patent No.: US 8,559,913 B2
(45) Date of Patent: Oct. 15, 2013

(54) EMERGENCY RESPONSE DEVICE FOR SUMMONING A RESPONDER AND ROUTING SAID RESPONDER TO A VICTIM

(75) Inventors: Jeroen Adrianus Johannes Thijs, Aachen (DE); Guido Muesch, Linnich (DE); Jens Muehlsteff, Aachen (DE); Robert Pinter, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 371 days.

(21) Appl. No.: 10/596,424

(22) PCT Filed: Dec. 16, 2004

(86) PCT No.: PCT/IB2004/052824
§ 371 (c)(1), (2), (4) Date: Jun. 6, 2007

(87) PCT Pub. No.: WO2005/060301
PCT Pub. Date: Jun. 30, 2005

(65) Prior Publication Data
US 2007/0218869 A1    Sep. 20, 2007

(30) Foreign Application Priority Data
Dec. 16, 2003 (EP) ..................... 03104720

(51) Int. Cl.
*H04M 11/04* (2006.01)
(52) U.S. Cl.
USPC ............ 455/404.2; 455/404.1; 607/32
(58) Field of Classification Search
USPC ................ 455/404.1, 404.2; 607/32
See application file for complete search history.

(56) References Cited

U.S. PATENT DOCUMENTS

| | | | | |
|---|---|---|---|---|
| 5,593,426 A | * | 1/1997 | Morgan et al. | 607/5 |
| 5,685,786 A | * | 11/1997 | Dudley | 473/407 |
| 6,292,687 B1 | * | 9/2001 | Lowell et al. | 600/515 |
| 6,292,698 B1 | * | 9/2001 | Duffin et al. | 607/32 |

(Continued)

*Primary Examiner* — Lester Kincaid
*Assistant Examiner* — Isaak R Jama

(57) ABSTRACT

The invention relates to an emergency response system. The emergency response system (10) comprises a central station (4) for receiving information about emergencies, whereby position information of a victim is provided and stored in a look-up table (6) of the central station (4). The central station addresses a list (7) of publicly available actuatable emergency response devices and selects a suitable device. The central station (4) transmits a trigger signal by means of a suitable communication network (3) to the selected remote actuatable emergency response device (14), which comprises communication means (13) for activating the signaling means (15) upon receipt of the trigger signal. Also, the actuatable emergency response device (14) comprises storage means (11) arranged to store the position information of the emergency response device and the provided position information of the victim. Upon receipt of a suitable signal from the communication means (13), the signaling means (15) start broadcasting a message arranged to attract as many potential emergency responders to the victim as possible. The emergency response device (14) comprises navigation means (20), arranged to provide a routing to the victim, which is being fed-back to the responder by the user interface. The invention further relates to an emergency response device and a method for summoning an emergency responder and for routing said responder to the victim.

20 Claims, 2 Drawing Sheets

(56) References Cited

U.S. PATENT DOCUMENTS

Figure 1:
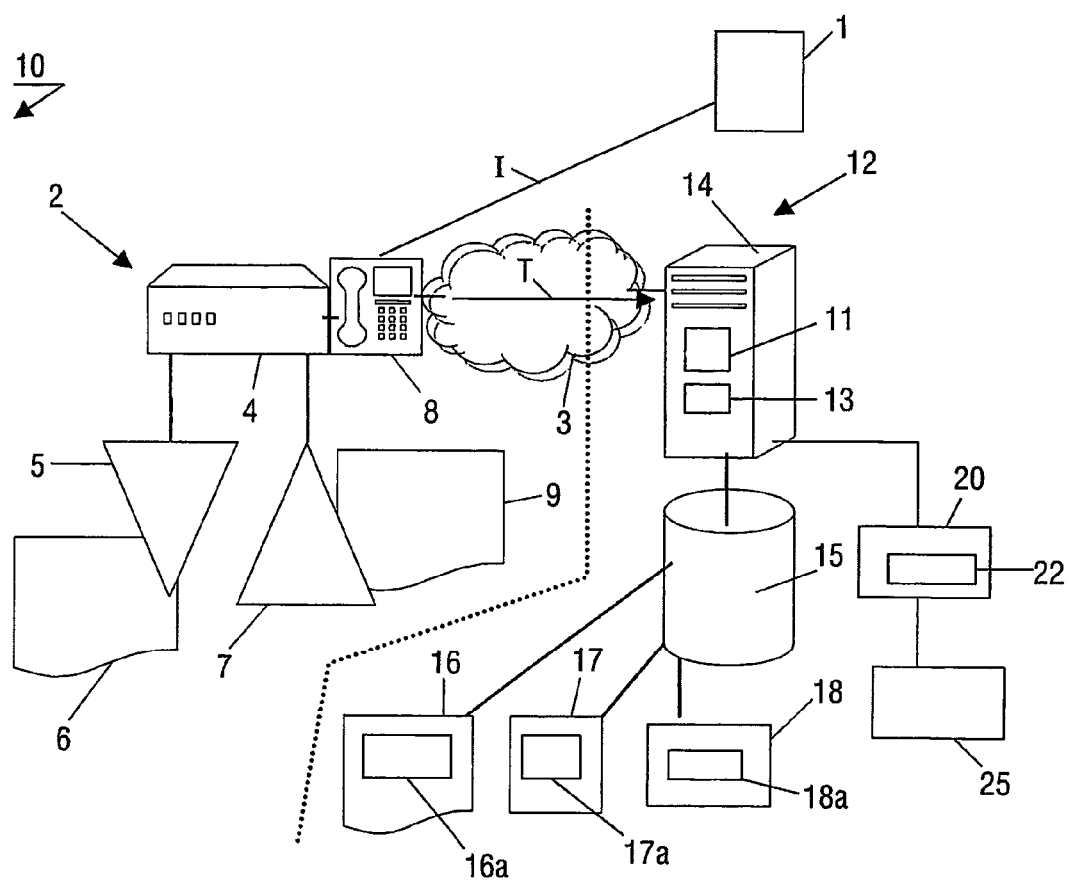

| | | | |
|---|---|---|---|
| 6,321,113 B1 * | 11/2001 | Parker et al. | 607/5 |
| 6,459,371 B1 * | 10/2002 | Pike | 340/539.1 |
| 6,493,581 B2 * | 12/2002 | Russell | 455/404.2 |
| 6,597,948 B1 * | 7/2003 | Rockwell et al. | 607/5 |
| 6,774,838 B2 * | 8/2004 | Sun | 342/357.57 |
| 7,120,488 B2 * | 10/2006 | Nova et al. | 607/2 |
| 7,289,029 B2 * | 10/2007 | Medema et al. | 340/573.1 |
| 2003/0233129 A1 * | 12/2003 | Matos | 607/5 |
| 2004/0128065 A1 * | 7/2004 | Taylor et al. | 701/201 |
| 2004/0266390 A1 * | 12/2004 | Faucher et al. | 455/404.1 |
| 2005/0143776 A1 * | 6/2005 | Brown | 607/4 |

* cited by examiner

EMERGENCY RESPONSE DEVICE FOR SUMMONING A RESPONDER AND ROUTING SAID RESPONDER TO A VICTIM

The invention relates to an emergency response system for summoning an emergency responder and for routing said responder to a victim, said system comprising:

a central station for actuating a remote emergency response device by transmitting a trigger signal to said emergency response device upon the signaling of a victim in the vicinity of said device;

an actuatable emergency response device.

The invention further relates to an emergency response device for summoning an emergency responder and for routing said responder to a victim upon receipt of a trigger signal indicating position information of the victim.

The invention still further relates to a method for summoning an emergency responder and for routing said responder to a victim, said method comprising the steps of:

providing an actuatable emergency response device;

actuating the emergency response device by transmitting a trigger signal to the emergency response device.

An embodiment of the emergency response system as set forth in the opening paragraph is known from U.S. Pat. No. 6,493,581. The known emergency response system is arranged for locating automatic defibrillators and potential operators thereof and for routing said operators to said defibrillators. For this purpose the known system comprises a locator arranged to determine a location of a victim suffering from a life threatening condition as well as to determine which defibrillator installed in a public place is suitable for the victim. Next, a potential operator to operate the selected defibrillator is chosen. For this purpose the known system comprises a list of potential operators who can be engaged in case a person is suffering from this life threatening condition. If the person is a registered heart-monitoring patient, the known system comprises an elaborate list of potential operators. For a non-registered person the potential operator is selectable from a list of people in charge of first-aid on premises where the incident is taking place. When the life-threatening incident is reported to the known emergency response system, the victim is first identified and the location thereof is established. From the location of the victim and/or other data a list of potential operators is compiled. The location of the victim is then entered by an operator of the emergency response system into a suitable computer program in order to determine the location of a suitable defibrillator. When a potential operator is contacted by the operator of the known emergency response system, the location of the suitable defibrillator and routing directions to reach the defibrillator and/or the victim are provided to the potential operator. In order to simplify the task of finding the defibrillator, the defibrillator is supplied with audible or visual alarm means arranged to attract the potential operator when he is approaching the defibrillator.

A first disadvantage of the known emergency response system resides in that a limited number of potential operators can be contacted. Even if a registered cardiac patient is suffering a heart attack, the listed responders may not be in the vicinity of the victim. Additionally, a listed person responsible for first-aid in a public building, may be substantially distant from a place of emergency so that it would take him a considerable amount of time to locate the victim and the defibrillator. Secondly, when the suitable defibrillator is located, the routing instructions how to reach the victim are audibly made available to the potential operator. In emergency situations, however, this may be insufficient as people are subjected to a considerable amount of stress.

It is an object of the invention to provide an emergency response system wherein the probability of locating a potential operator in the vicinity of the victim is substantially increased and the time span for finding the victim is substantially decreased.

To this end, in the emergency response system according to the invention, the trigger signal comprises position information of the victim, and the actuatable emergency response device comprises:

communication means arranged to activate a signaling means upon receipt of the trigger signal;

signaling means arranged to broadcast a message for summoning an emergency responder to the victim;

navigation means arranged to determine a routing of the emergency responder to the victim based on the position information of the victim and position information of the emergency response device;

user interface arranged to feedback the routing to the emergency responder.

According to the technical measure of the invention, the emergency response system is arranged to provide position information of the victim to the emergency response device. In case the victim is a registered person, for example a cardiac patient wearing a monitoring system, the central station will receive an alarm together with position information of the victim. Using a suitable database the central station will determine where the victim is located. In case the victim is located in a public place, the central station will select a suitable actuatable emergency response device, which is preferably situated in the vicinity of the victim. The central station will then actuate the remote emergency response device by means of a trigger signal comprising the position information of the victim. Upon receipt of the trigger signal by means of the communication means of the emergency response device, the signaling means is activated. The signaling means is arranged to attract and to summon as many possible operators of the emergency response device as possible, thus maximizing the chance of locating a person for operating the emergency response device in a short time. Due to the fact that the suitable emergency response device is operable by any capable person, the chance of finding one in a public place is sufficiently high. In order to develop the routing of the emergency responder to the victim, the emergency response device comprises navigation means which is arranged to determine a suitable routing based on the coordinates of the victim and a pre-known dwell location of the emergency response device. The pre-known dwell location of the emergency response device can be determined in real-time using for example a GPS receiver. Alternatively, the pre-known dwell location of the emergency response device can be pre-stored and can be made available to the navigation means on request. Preferably, the pre-stored position information is stored within the emergency response device. This embodiment is advantageous as the satellite connection is established only during navigation, thus reducing power consumption by the emergency response device. When the emergency responder is summoned, he can easily find the victim provided with the calculated routing information, which is made available to the emergency responder by the user-interface of the emergency response device. In this way, according to the insight of the invention, an automatic emergency response system is provided, wherein the summoning of the emergency responder from an increased pool of potential responders is carried out in an automatic way. When the emergency responder reacts, he is routed to the victim in a fully automated fashion, thus minimizing the time lapse before aid is given to the victim.

In an embodiment of the emergency response system according to the invention, the actuatable emergency response device further comprises detection means arranged to activate the navigation means upon detection of an interaction with the emergency response device.

It is considered to be preferable to provide the emergency response device with the detection means for detecting an action of the emergency responder on the device. For example, picking up of the device from its cell, pressing a suitable button, releasing a suitable clutch holding the device in the cell can all be used for designing a suitable detection means, which is arranged to activate the navigation means upon detection of a corresponding interaction with the emergency response device. In these cases the navigation means are activated only when someone picks up the device. This embodiment causes the energy consumed by the emergency response device to be reduced considerably since communication with a positioning system, for example a GPS, is initiated only when the routing is to be calculated and made available to the user.

The emergency response device according to the invention comprises:
  communication means arranged to receive the trigger signal and to activate a signaling means upon receipt of the trigger signal;
  signaling means arranged to broadcast a message for summoning the emergency responder to the victim;
  navigation means arranged to determine a routing of the emergency responder to the victim based on the position information of the victim and position information of the emergency response device;
  user interface arranged to feedback the routing to the emergency responder.

The emergency response device according to the invention presents a self-contained unit for locating the victim, summoning the emergency responder and directing the emergency responder to the victim. In order to summon the emergency responder, the emergency response device according to the invention is arranged to activate its signaling means upon receipt of the trigger call indicating that there is a victim in the vicinity of the device. The signaling means is arranged to broadcast a message attracting all people in the vicinity of the device. This increases the chance of finding a responder in a short time. When the responder manifests himself, for example by picking up the emergency response device, the routing to the victim is calculated by the navigation means of the device and is made available to the emergency responder by means of a suitable user interface. Preferably, the user interface is arranged to supply a visual scheme of the routing together with corresponding audible support.

In an embodiment of the emergency response device according to the invention, the navigation means comprises a detection means arranged to activate the navigation means upon detection of an interaction with the emergency response device.

It is found to be advantageous to reduce the energy consumption of the emergency response device by providing it with a suitable detection means which is arranged to activate the navigation means only upon detection of an interaction of the emergency responder with the device. Examples of suitable detection means comprise a button or any other interface to be actuated by the responder, or a movement sensor integrated in the device which is arranged to activate the navigation means upon detection that the device is being picked up.

In a further embodiment of the emergency response device according to the invention, the communication means comprises a wireless telecommunication means. It is found to be advantageous to provide the emergency response device with a wireless communication means, especially if the device is to be located in places where no cable connection is present. For example, in woods, at sea, in airplanes or ships, etc. it is advantageous to have a suitable emergency response device which is operable by means of a wireless connection. Examples of wireless connection comprise mobile telephony, satellite communication and the like. Suitable embodiments of emergency response devices comprise medical apparatus, like a first-aid kit, a defibrillator, an oxygen supply vessel, a respiration machine, etc. Also, the emergency response device can be of a general purpose type, like a fire extinguisher, or the like.

In a still further embodiment of the emergency response device the communication means comprises a wired telecommunication means, said wired telecommunication means comprising at least one of a computer modem or a fixed line telephone unit.

It is found to be particularly advantageous to provide the emergency response device with a computer modem. In this case all data exchange can take place promptly, the input data being supplied by means of an incoming call. If the communication means comprises a fixed line telephone unit, the input data is preferably fed in by means of a coded message transmitted during a telephone connection.

In a still further embodiment of the emergency response device, the signaling means comprises a wireless communication unit arranged to contact further wireless communication units.

It is found to be particularly advantageous to provide message broadcasting by means of a wireless communication protocol. There are several envisaged possibilities for connecting to other wireless communication units. First, the communication means can be arranged to send the message to another GSM unit by means of a Cell Broadcast, which sends the message to every mobile phone user in the same cell. Usually, cells in the GSM system range from 10 m in cities to 10 km in rural areas. For this purpose, the emergency response device is provided with a GSM module that can send messages using Cell Broadcast. Secondly, it is possible to connect to other mobile devices via Bluetooth or another short-range communication technology, which has a range of around 10 meters and can contact nearby mobile devices by initiating a connection to a nearby mobile device and by sending a message to this mobile device. Receipt of the message will preferably trigger an audible alarm to alert the user of the mobile device that the message has arrived. By this technical measure the number of possible emergency responders is substantially increased.

In a still further embodiment of the emergency response device according to the invention, the signaling means comprises a loudspeaker arranged for broadcasting a verbal message.

For densely occupied areas like airports, grocery stores, and/or for areas where usage of wireless facilities is not recommended, like in theatres, etc. it is found to be useful to broadcast the message by means of a verbal transmission using a loudspeaker arranged in the emergency response device.

A method according to the invention comprises the steps of:
  providing a trigger signal comprising position information of the victim;

broadcasting a message by means of the emergency response device for summoning an emergency responder in the vicinity of the emergency response device;

determining the routing of the emergency responder to the victim;

providing feedback of the routing to the emergency responder.

These and other aspects of the invention will be explained in further detail with reference to Figures.

FIG. 1 presents a schematic view of an embodiment of an architecture of the emergency response system according to the invention.

Figure 2:
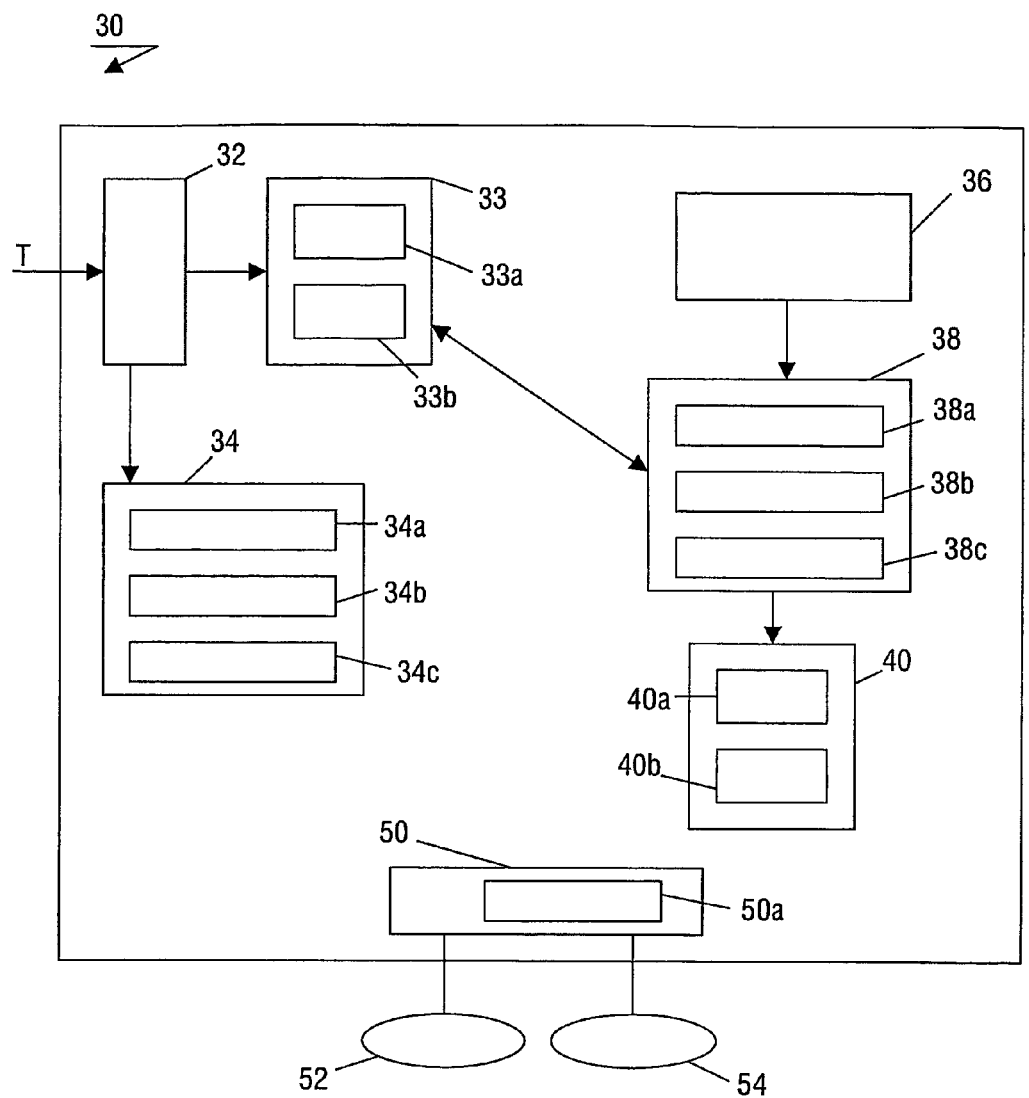

FIG. 2 presents a schematic view of an embodiment of an emergency response device according to the invention.

FIG. 1 presents a schematic view of an embodiment of an architecture of the emergency response system according to the invention. The emergency response system 10 according to the invention can be imaginarily divided into two parts, a central side 2 and a remote side 12. The central side 2 comprises a central station 4 to which emergencies of a certain type are forwarded. For example, the central station 4 can be arranged to manage medical emergencies. A preferred medical emergency is a cardiac emergency taking place outside a residence of the victim. Alternatively, the central station 4 can be arranged to manage a further emergency, for example a fire alarm. Alternatively, the central station 4 can be arranged to manage another type of emergency, for example a traffic accident. The operation of the emergency response system in all of the above cases is similar and will be explained by means of an example of the cardiac emergency.

In case a victim suffering a life threatening cardiac emergency is detected, a corresponding indication I is forwarded to the central station 4. In case the victim is wearing a suitable monitoring system 1, the indication I is generated automatically by the monitoring system 1 and is forwarded to the central station 4, preferably using suitable telecommunication means 8. The central station 4 identifies the victim, for example by using a unique code supplied by the monitoring system 1 together with the indication I. The monitoring system 1 is preferably arranged to provide position information of a location of the victim together with the emergency indication I. The provided position information of the victim is stored in a look-up table 6 of the central station 4. Alternatively, a person detecting the victim can call the central station. In this case an operator of the central station (not shown) can interview such person to get position information about the victim, which is then stored in the look-up table 6.

In the case of such an event, when the position information of the victim is received, the central station addresses a list 7 of publicly available actuatable emergency response devices and selects a suitable device, preferably an automated external defibrillator. The selection is based on a comparison between the pre-stored position information of the available emergency response device, stored in a further look-up table 9, and the position information of the victim. Preferably, the device closest to the victim is selected. When the remote-actuatable emergency response device is selected, the central station 4 transmits a trigger signal T to the selected remote-actuatable device 14 by means of a suitable communication network 3. The actuatable emergency response device 14 comprises communication means 13 arranged to actuate the signaling means 15 upon receipt of the trigger signal. An example of a suitable communication means comprises a computer modem, a wired or wireless telecommunication port, etc. Also, the actuatable emergency response device 14 comprises storage means 11 arranged to store the pre-known position information of the emergency response device and the provided position information of the victim. Upon receipt of a suitable signal from the communication means 13, the signaling means 15 start broadcasting a message arranged to attract as many potential emergency responders to the victim as possible. Different embodiments of an operation of the signaling means 15 are envisaged. First, the signaling means 15 can comprise means 16 for broadcasting a verbal message, for example a loudspeaker. The verbal message can be a pre-recorded standard message, or it can be generated in real-time by means of a suitable speech generator 16a. In case the victim is suffering from a cardiac emergency and the emergency response device is an automated external defibrillator, a corresponding message can comprise: "There is a cardiac victim in the neighborhood, please pick up defibrillator and proceed to the victim". Any other suitable messages can also be generated. This embodiment is particularly useful for densely populated areas, like an airport hall, a supermarket, a railway station, an educational establishment, a hospital, etc.

Alternatively or additionally, the signaling means 15 can be provided with a visual indication means 18, which is arranged to provide a visual signal, for example a blinking light for purposes of further attraction of potential emergency responders. It is also possible that the visual indication means are arranged in a suitable word or a phrase 18a, which can be read from a distance. This feature further increases the awareness of bystanders that prompt assistance is required.

Alternatively or additionally, the signaling means 15 comprises wireless communication means 17, arranged to contact further wireless communication units, which are preferably located in the vicinity of the wireless communication means 17. This embodiment is particularly useful for isolated locations, where the chance of locating a person in the direct vicinity of the emergency response device is reduced. Preferably, the wireless communication means 17 is a mobile telephony unit operating in a GSM format, which is arranged to transmit a pre-defined message 17a to all wireless communication units that are present in the same geographically confined area, called a cell. By doing this all holders of the operating mobile telephony units in a certain range around the emergency response device are contacted and can be summoned to operate the emergency response device in order to assist the victim.

When the emergency responder is summoned and a person has responded, he approaches the emergency response device and takes it from its dwell position. The emergency response device 14 comprises navigation means 20, arranged to provide a routing to the victim. Preferably, the navigation means 20 is arranged to communicate with a suitable positioning system, for example a GPS, in order to calculate the routing using the position information of the device and the position information of the victim. Preferably, the position information of the emergency response device is stored in a corresponding look-up table of the storage means 11. Alternatively, the position information of the emergency response device can be obtained on request using a suitable GPS module. The routing is preferably calculated by means of a suitable computer program 22 provided with the navigation means 20. Suitable examples of the navigation system and the computer program are known per se in the art and will not be explained in detail. In order to simplify the task of the emergency responder, the emergency response device comprises a user interface 25, which is arranged to feedback the routing to the emergency responder. Preferably, the user interface 25 comprises a suitable display on which the routing instructions are projected. Additionally, voice instructions can be initiated. This feature is particularly useful in case the emergency responder has to use a vehicle to find the victim.

FIG. 2 presents a schematic view of an embodiment of an emergency response device according to the invention. In this example an automated external defibrillator 30 is selected as the emergency response device. The automated external defibrillator (AED) 30 is arranged to be actuated by an external trigger signal T for purposes of summoning a potential emergency responder located in the vicinity of the AED. For this purpose the AED is provided with communication means 32 arranged to receive the trigger signal T. In practice, the trigger signal T is usually sent by a central unit (not shown) arranged for managing cardiac emergencies. The central unit will have the position information of the victim, which will be made available to the AED 30 by means of the trigger signal T or together with the trigger signal T. In case block dialing is used for triggering purposes, the position information can be provided as a code, which is then decoded by the communication means 32 and the position information thus determined is stored in the storage means 33 of the AED 30. Preferably, the storage means 33 comprises a look-up table 33a designated for the position information of the victim. The position information of a dwell location of the AED 30 is stored in a further look-up table 33b. The position information of the AED can be pre-stored or can be obtained in real-time using a suitable GPS receiver and then be stored in the further look-up table 33b.

Upon receipt of the trigger signal T, the communication means 32 activate the signaling means 34 for purposes of attracting potential emergency responders to pick up the AED. Different embodiments of the signaling means 34 are envisaged. First, the signaling means 34 can comprise means 34a for broadcasting a verbal message, for example a loudspeaker. The verbal message can be a pre-recorded standard message, or it can be generated in real-time by means of a suitable speech generator. Embodiments of suitable speech generators are known per se in the art. A suitable message may be: "There is a cardiac victim in the neighborhood, please pick up defibrillator and proceed to the victim". Any other suitable messages can also be generated. This embodiment is particularly useful for densely populated areas, like an airport hall, a supermarket, a railway station, an educational establishment, a hospital, etc.

Alternatively or additionally, the signaling means 34 can be provided with a visual indication means 34b, which is arranged to provide a visual signal, for example a blinking light for purposes of further attraction of potential emergency responders. It is also possible that the visual indication means is arranged in a word or a phrase, which can be read from a distance. This feature further increases awareness of bystanders that prompt assistance is required.

Alternatively or additionally, the signaling means 34 comprises wireless communication means 34c, arranged to contact further wireless communication units, which are preferably located in the vicinity of the AED 30. This embodiment is particularly useful for isolated locations, where the chance of locating a person in the direct vicinity of the emergency response device is reduced. Preferably, the wireless communication means 34c is a mobile telephony unit operating in a GSM format, which is arranged to transmit a pre-defined message to all wireless communication units present in the same geographically confined area, called a cell. As a result of such a broadcast, all holders of operating mobile telephony units in a certain range from the emergency response device are contacted and can be summoned to operate the emergency response device in order to assist the victim.

When the emergency responder is found, he picks up the AED 30 and proceeds to the victim. The AED 30 is provided with the navigation means 38, which is arranged to calculate the routing information to the victim. The routing information is calculated based on the position information stored in the look-up tables 33a, 33b, using a suitable calculation algorithm 38b provided with the navigation means 38. Preferably, the calculation algorithm 38b addresses city or landscape maps, building plans and all other helpful information, which is preferably stored in a database 38c of the navigation means. In order to update the routing as the emergency responder moves, the navigation means 38 comprises a mobile positioning system 38a, for example a GPS which updates the coordinates of the AED 30 with time. As communicating with an external positioning system involves a considerable power consumption, it is preferable to provide the AED 30 with an actuatable navigation means 38, which is activated only in the case of an interaction with the AED by the emergency responder. For this purpose the AED 30 is provided with a detection means 36, which is arranged to detect the interaction. An example of a suitable detection means comprises a button (not shown), preferably arranged on a cover of the AED 30. Alternatively, the detection means 36 can comprise a movement detector (not shown), which is arranged to activate the navigation system when it is detected that the AED is picked up. Alternatively, the detection means 36 can comprise a releasable clutch (not shown), which is released when the AED is removed from its dwell location. The releasable clutch can be arranged to operate a suitable switch to power the navigation means 38. Upon their activation, the navigation means 38 calculates the routing to the victim.

In order to simplify the task of finding the victim, the AED 30 comprises a user interface 40 arranged to feedback the routing instructions to the emergency responder. For this purpose the user interface 40 preferably comprises a display 40a on which a map, a building plan or instruction can be projected. It is found to be advantageous to provide the user interface with a voice control 40b, which is arranged to feedback the routing instructions to the emergency responder as he proceeds. This feature is particularly useful when the emergency responder is in a moving vehicle.

When the emergency responder reaches the victim, he applies the AED to the victim. For this purpose the AED 30 is provided with a defibrillation logic 50, which is arranged to guide the emergency responder through all steps of delivering a defibrillation shock. Preferably, the defibrillation logic 50 comprises a suitable user interface 50a which provides instructions to the emergency responder. Usually, prior to delivering the defibrillation shock, the emergency responder is asked to place the electrodes 52, 54 on the chest of the victim for measuring the heart rhythm. In case the defibrillation logic 50 determines that the condition of the victim is defibrillatable, a corresponding message is provided to the emergency responder and a defibrillation shock is applied.

Although the invention has been described with reference to preferred embodiments thereof, it is to be understood that these are not limitative examples. Thus, various modifications may be apparent to those skilled in the art, without departing from the scope of the invention, as defined by the claims. The invention can be implemented by means of both hardware and software, and several 'means' may be represented by the same item in hardware. Any reference signs do not limit the scope of the claims.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for summoning an emergency responder and for routing said responder to a victim, said method comprising the steps of:
   providing an actuatable emergency response device;
   actuating the emergency response device by transmitting a trigger signal to the emergency response device, said trigger signal comprising position information of the victim;
   broadcasting a message by a signaling unit of the emergency response device for summoning an emergency responder in a vicinity of the emergency response device;
   activating by the emergency response device a navigation unit of the emergency response device in response to the emergency response device detecting an interaction between the emergency responder and the emergency response device;
   determining a routing of the emergency responder to the victim with the activated navigation unit of the emergency response device;
   providing feedback of the routing to the emergency responder on a user interface of the emergency response device.

2. The method according to claim 1, wherein the emergency response device is an automated external defibrillator.

3. The method according to claim 2, wherein the navigation unit is activated in response to the defibrillator being lifted.

4. The method according to claim 1, wherein the actuatable emergency response device is one of a plurality of publicly available emergency response devices.

5. The method according to claim 4, further including:
   selecting one of the plurality of publicly available actuatable emergency response devices based on a comparison between pre-stored position information of the plurality of publicly available emergency response devices and the position information of the victim.

6. The method according to claim 1, wherein the routing of the emergency responder to the victim is based on the position information of the victim and position information of the emergency response device and is not determined until an interaction between the emergency responder and the emergency response device is detected.

7. The method according to chum 1, wherein the navigation unit stores a floor plan of at least is portion of a building in which the emergency response device is located and the provided feedback displays at least a portion of the floor plan, as part of the routing fed back to the emergency responder.

8. An emergency response system for summoning an emergency responder and for routing said responder to a victim, said system comprising:
   a central station for actuating a remote emergency response device by transmitting a trigger signal to said device upon receiving a victim signal indicative of a victim in need of said emergency response device, the central station including a look-up table of pre-stored position information of publicly available actuatable emergency response devices, wherein the central station selects one or more emergency response devices based on emergency response device position and automatically transmits the trigger signal including victim position information to the selected one or more emergency response devices, the selection of emergency response devices being based on a comparison between pre-stored position information of available emergency response devices and the position information of the victim, and the selectable one or more emergency response devices comprises:
   communication unit which receives the trigger signal and activates a signaling unit upon receipt of the trigger signal to broadcast a message for summoning emergency responders to the emergency response device;
   a navigation unit which in response to detecting an inter of the emergency responder with the emergency response device determines a route for the emergency responder between the emergency response device, and the victim based on the victim position information and the emergency response device position; and
   a user interlace which feeds back the route to the emergency responder.

9. The system according to claim 8, wherein the emergency response device further includes:
   an automatic external defibrillator.

10. The system according to claim 9, wherein the user interface includes;
   a display which displays instructions to guide the emergency responder along the route and through stops of delivering a defibrillation shock.

11. The system according to claim 8, wherein the user interface includes:
   a display configured to project the routing 0.1 instructions and a map of the routing instructions.

12. The system according to claim 8, wherein there are a plurality of emergency response devices and the central station transmits the trigger signal to more than one of the emergency response devices.

13. The system according to claim 8, wherein the routing of the emergency responder to the victim based on the position information of the victim and position information of the emergency response device is not determined until an interaction between the emergency responder and the emergency response device is detected.

14. An emergency response device for summoning an emergency responder and for routing said responder to a victim upon receipt of a trigger signal indicating position information of the victim, said emergency response device comprising:
   a communication unit configured to receive the trigger signal and to activate a signaling unit upon receipt of the trigger signal;
   the signaling unit being configured to broadcast a message for summoning an emergency responder to the victim;
   a navigation unit configured to determine a routing of the emergency responder to the victim based on the position information of the victim and position information of the emergency response device;
   a user interface configured to feed back the routing to the emergency responder; and
   a detector of the emergency response device configured to activate the navigation unit in response to detecting an interaction between the emergency responder and the emergency response device, such that the routing of the emergency responder to the victim based on the position information of the victim and position information of the emergency response device is not determined until an interaction between the emergency responder and the emergency response device is detected.

15. The device according to claim 14, wherein the communication unit is configured to communicate by wireless telecommunication.

16. The device according to claim 14, wherein the signaling unit includes:
   a wireless communication unit configured to contact all wireless communication units located in a vicinity of the wireless communication.

17. The device according to claim 14, wherein the signaling unit includes:
   a loud speaker configured for broadcasting a verbal message.

18. The device according to claim 14, wherein the device further includes:
   an automated external defibrillator.

19. The device according to claim 14, wherein the navigation unit stores a floor plan of at least a portion of a building in which the emergency response device is located and the user interface displays at least a portion of the to plan as part of the muting fed back to the emergency responder.

20. The device according to claim 14, wherein the detector include:
   a movement detector configured to detect when the emergency response device is picked up by the emergency responder.

* * * * *